United States Patent [19]

Cibulskas et al.

[11] Patent Number: 4,997,759

[45] Date of Patent: Mar. 5, 1991

[54] USE OF BLENDS OF MANNICH ACRYLAMIDE POLYMERS AND DIMETHYLDIALLYLAMMONIUM HALIDE POLYMERS FOR FLOCCULATING ENZYME BROTH STREAMS

[75] Inventors: Algird S. Cibulskas, Stamford, Conn.; Henri R. Asbell, Martinez, Calif.

[73] Assignee: American Cyanamid Company, Stamford, Conn.

[21] Appl. No.: 474,875

[22] Filed: Feb. 5, 1990

[51] Int. Cl.$^5$ .............................................. C12N 9/50
[52] U.S. Cl. ................................................... 435/219
[58] Field of Search ......................................... 435/219

[56] References Cited

U.S. PATENT DOCUMENTS 3,442,764  5/1969  Young et al. .................. 435/219
4,508,825  4/1985  Kim et al. ..................... 435/219

FOREIGN PATENT DOCUMENTS 227677  11/1985  Japan ............................ 435/219
962302   9/1982  U.S.S.R. ....................... 435/219

Primary Examiner—J. E. Evans
Attorney, Agent, or Firm—Frank M. Van Riet

[57] ABSTRACT

Blends of Mannich acrylamide polymers and dimethyldiallylammonium halide polymers have been found to be superior flocculants for enzyme broth streams yielding higher solid compaction and greater supernatant clarities than the use of either polymer alone.

10 Claims, No Drawings

USE OF BLENDS OF MANNICH ACRYLAMIDE POLYMERS AND DIMETHYLDIALLYLAMMONIUM HALIDE POLYMERS FOR FLOCCULATING ENZYME BROTH STREAMS

BACKGROUND OF THE INVENTION

The production of enzymes by fermentation has been carried out for many years. Fermentation is usually carried out in stainless steel equipment i.e. mixing and blending tanks, and seed and main fermentators. Constant temperature, automatic foam and pH controllers and air purifiers are employed since the absence of foreign microorganisms is essential. Tap water is generally combined with the media ingredients and enzyme recovery begins as soon as fermentation is terminated. The medium is cooled and centrifuges are used to remove bacteria and large insolubles from the supernatant followed by filters to separate smaller particles. Enzyme is concentrated and removed from the filtrate by the addition of a precipitating agent. The precipitate is then further treated by additional filtering and drying etc. and is then standardized such as by using sodium chloride.

Proteases are enzymes which have been found to be particularly useful in industrial areas including cheese making, meat tenderizing, bread baking, beer haze elementation, digestive aid preparations, garment cleaning, pharmaceutical preparation and the like. Those proteases produced by cultivation can be used as food additives.

Characteristic of the protease enzyme broth is the formation of a suspension that does not settle. Upon centrifugation of a sample in a test tube, solids will be deposited in the lower 70% of the test tube and only the upper 30% of the tube will be clear supernatant solution.

One of the most difficult problems involving enzyme production is the isolation of the enzyme from its broth. Although many flocculating agents have been used for the precipitation of enzyme broths, most have suffered from some disability which renders the agent less attractive commercially. Examples of flocculants used commercially include epichlorohydrindimethylamine condensation products cross-linked with diethylenetriamine/dicyanamide; Mannich acrylamide polymers and polydimethyldiallylammonium halides. These additives, although tolerable, ofttimes fail to result in the isolation of the enzyme sufficiently e.g. the solids are not compacted; the supernatant has poor clarity, etc. Thus, the search for more effective flocculants is continuing and the discovery of useful materials which do not suffer from the deficiencies of the existing commercial flocculants would satisfy a long felt industrial need.

SUMMARY OF THE INVENTION

The present invention relates to a process for precipitating aqueous enzyme broths comprising using, as the flocculating agent, a blend of a Mannich acrylamide polymer and a diallyldimethylammonium halide polymer, which blend has been found to provide more effective flocculation of precipitate than either of these known flocculants alone.

DESCRIPTION OF THE INVENTION INCLUDING PREFERRED EMBODIMENTS

This invention relates to a process for precipitating an aqueous enzyme broth which comprises adding to said broth a flocculant comprising a blend of (1) a Mannich acrylamide polymer and (2) a dimethyldiallylammonium halide polymer.

The blends are composed of the two polymers (1); (2) in a ratio of 3:1 to 1:30, by weight, real polymer solids, respectively, preferably 1:1.5 to 1:7, respectively.

The Mannich acrylamide polymers are generally well known in the art, examples thereof being disclosed in U.S. Pat. No. 4,137,164, hereby incorporated herein by reference. Generally, these polymers are homopolymers of acrylamide or copolymers thereof with such commoners as acrylonitrile, methacrylamide, acrylic acid etc. in amounts up to about 50%, preferably 5-50% of the resultant copolymer. The polymers have molecular weights ranging from about 10,000 to about 3,000,000 and are chemically modified to provide dimethylaminomethyl groups to the extent that the polymer contains 25-100 mol percent of these groups, preferably at least 40 mol percent.

The dimethyldiallylammonium halide (DADM) polymers are likewise known in the art, examples thereof being disclosed in U.S. Pat. No. 4,092,467, hereby incorporated herein by reference. These polymers are homopolymers of DADM or copolymers thereof with such monomers as acrylamide, vinyl pyrrolidone, etc. in amounts up to about 20% of the resultant polymer. These polymers have Intrinsic Viscosities ranging from about 0.1-4.00 deciliters per gram. The halide can be chloride, fluoride, bromide or iodide.

The polymer blend may be added to the enzyme broth as such or the two polymers may be added individually but as near the same time as possible, since the enhanced benefit of the polymers is attributed to their presence in the broth coincidentally. The amount of the blend added to the broth is that effective to produce the clearest supernatant and achieve the highest solid compaction as possible. Generally, amounts ranging from about 10 to 100 grams of polymer blend per liter of broth, preferably from about 25-75 grams per liter, is effective, although higher or lower amounts may be useful in specific instances.

The following examples are set forth for purposes of illustration only and are not to be construed as limitations on the present invention. Products A and B are set forth in the following tables, with respect to the amounts employed, as 0.065% aqueous polymer solutions while Product C is expressed as a 20.0% aqueous polymer solution. Clarity is measured by UV absorbance at 660 microns.

In the following examples, the Mannich acrylamide polymers employed are each Mannich polyacrylamide of 70% aminomethylation and are further designated as follows:

| Product | Percent Solids | Brookfield Viscosity-cps |
|---------|---------------|--------------------------|
| A | 5.9-6.4% | 26,000-34,000 |
| B | 5.5-6.1 | 34,000-46,000 |

The dimethyldiallylammonium halide polymer is polydimethyldiallyammonium chloride further designated as follows:

| Product | Percent Solids | Intrinsic Viscosity-cps |
| --- | --- | --- |
| C | 19.5–20.5 | 2.0–3.5 |

In order to test the effectiveness of various polymers in flocculating enzyme broths, the following test procedure is utilized: To 5 ml of broth in a 15 ml clinical, graduated centrifuge tube are added 5 ml. samples of various concentrations of the polymer solutions. Each sample is mixed by inverting the stoppered clinical tube 20 times, the clinical tube is then centrifuged for 5 minutes and the volume of the compacted enzyme is visually measured. The lower the value, the better. In addition, the clarity of the supernatant is measured by UV absorbance at 660 microns. A value of 0.3–0.4% is acceptable and below 0.1 is superior.

Table I is a measure of the effect of single polymer flocculants on the precipitation of enzyme broths. It is a comparative table showing that although Products A, B and/or C individually may perform effectively with regard to compaction (% volume solids) or clarity, the flocculants alone fail to perform satisfactorily as regards both criteria.

TABLE I

Effect of Single Polymer Flocculants on The Flocculation of Enzyme Broth

| Exp. No. | Flocculant | g/l Flocculant | No. of Tube Inversions | Centrifuge 5 Minutes % Volume Solids | Clarity of Supernatant 660 Microns |
| --- | --- | --- | --- | --- | --- |
|  | None | — | — | 72 | poor |
| 1 | C 1st run | 5 | 20 | 28 | 1.58 |
|  |  | 10 | 20 | 27 | 0.622 |
|  |  | 15 | 20 | 26 | 0.477 |
|  |  | 20 | 20 | 26 | 0.438 |
|  |  | 25 | 20 | 27 | 0.393 |
| 2 | C 2nd run | 10 | 20 | 28 | — |
|  |  | 10 | 20 | 29 | 0.879 |
|  |  | 15 | 20 | 24 | 0.338 |
|  |  | 20 | 20 | 26 | 0.306 |
|  |  | 25 | 20 | 26 | 0.245 |
| 3 | C 3rd run | 5 | 20 | 28 | 1.14 |
|  |  | 10 | 20 | 27 | 0.432 |
|  |  | 15 | 20 | 24 | 0.303 |
|  |  | 20 | 20 | 24 | 0.272 |
|  |  | 25 | 20 | 25 | 0.251 |
| 4 | C 4th run | 5 | 20 | 31 | 0.649 |
|  |  | 10 | 20 | 31 | 0.577 |
|  |  | 15 | 20 | 31 | 0.299 |
|  |  | 20 | 20 | 31 | 0.240 |
|  |  | 25 | 20 | 31 | 0.232 |
| 5 | A | 15 | 20 | — | — |
|  |  | 25 | 20 | 18 | 1.72 |
|  |  | 35 | 20 | 18 | 0.272 |
| 6 | A | 15 | 20 | 20 | 0.253 |
|  |  | 17.5 | 20 | 20 | 0.225 |
|  |  | 20 | 20 | 19 | 0.154 |
| 7 | B 1st run | 20 | 20 | 15 | — |
|  |  | 30 | 20 | 15 | 0.116 |
|  |  | 40 | 20 | 17 | 0.258 |
| 8 | B 2nd run | 15 | 20 | — | — |
|  |  | 25 | 20 | 18 | 1.68 |
|  |  | 35 | 20 | 18 | 0.253 |
| 9 | B | 15 | 20 | 21 | 0.796 |
|  |  | 17.5 | 20 | 22 | 0.298 |
|  |  | 20 | 20 | 20 | 0.184 |

Table II reflects the unexpectedly superior result achieved when using blends of C and B polymers on an enzyme broth. As can be seen, in this instance, as the blend approaches a ⅓ mixture, the compaction and the clarity are drastically improved.

TABLE II

Improved Compaction and Clarity of Supernatant with Polymer Blends

| Exp. No. | Flocculant | Ratio | g/l | No. of Tube Inversions | Centrifuge 5 Minutes % Volume Solids | Clarity of Supernatant 660 Microns |
| --- | --- | --- | --- | --- | --- | --- |
| 10 | C |  | 15 | 20 | 23 | 0.384 |
|  |  |  | 20 | 20 | 23 | 0.309 |
|  |  |  | 25 | 20 | 24 | 0.319 |
| 11 | B |  | 20 | 20 | 15 | Poor |
|  |  |  | 30 | 20 | 15 | 0.116 |
|  |  |  | 40 | 20 | 17 | 0.258 |
| 12 | B/C | 1.3/1 | 20 | 20 | 18 | 0.588 |
|  |  |  | 30 | 20 | 17 | 0.270 |
|  |  |  | 40 | 20 | 18 | 0.614 |
| 13 | B/C | 1/3 | 15 | 20 | 17 | 0.218 |
|  |  |  | 20 | 20 | 19 | 0.101 |
|  |  |  | 25 | 20 | 19 | 0.093 |

Examples 14–20 of the Table III represent comparative results as in Table II using Product A instead of Product B. As can be seen, the blends result in clarities superior to either polymer alone. The compaction values are not as good for the blends as Product A alone; however, the excellent overall results achieved by the blends are clearly shown.

In Examples 21–26 varying ratios of Product B to Product C are shown to be excellent as the level of Polymer B increases, especially with regard to the compaction. Example 24, at 35 g/l results in the outstanding value of 0.069 with a compaction value of 20.

The blends of A/C and B/C (Examples 27–32) show exceptional clarity in conjunction with acceptable compaction, compare Example 9.

Examples 33–43 form further support for the unexpected synergistic results achieved by the blends in that compaction falls well within the accepted range and increasingly superior clarity at dosage of 10–20 g/l are set forth.

An enzyme fermentation broth is treated in Examples 44–52 with the benefits of the polymer blends being clearly evident. Examples 53–62 reflect the same inventive trend.

TABLE III

Polymer Blend Ratios vs. Effect on Compaction and Supernatant Clarity

| Exp. No. | Flocculant | Ratio | g/l | No. of Tube Inversions | Centrifuge 5 Minutes % Volume Solids | Clarity of Supernatant 660 Microns |
| --- | --- | --- | --- | --- | --- | --- |
| 14 | C | — | 15 | 20 | 30 | 0.824 |
|  |  |  | 25 | 20 | 28 | 0.465 |
|  |  |  | 35 | 20 | 29 | 0.359 |
| 15 | A | — | 15 | 20 | — | — |
|  |  |  | 25 | 20 | 18 | 1.72 |
|  |  |  | 35 | 20 | 18 | 0.275 |
| 16 | A/C | 3/1 | 15 | 20 | 18 | 0.609 |
|  |  |  | 25 | 20 | 20 | 0.629 |
|  |  |  | 35 | 20 | 20 | 0.128 |
| 17 | A/C | 1/1.5 | 15 | 20 | 20 | 0.955 |
|  |  |  | 25 | 20 | 20 | 0.230 |
|  |  |  | 35 | 20 | 20 | 0.190 |
| 18 | A/C | 1/3 | 15 | 20 | 20 | 0.472 |
|  |  |  | 25 | 20 | 20 | 0.172 |
|  |  |  | 35 | 20 | 20 | 0.131 |
| 19 | A/C | 1/7 | 15 | 20 | 20 | 0.263 |
|  |  |  | 25 | 20 | 22 | 0.153 |
|  |  |  | 35 | 20 | 23 | 0.150 |
| 20 | A/C | 1/30 | 15 | 20 | 24 | 0.290 |
|  |  |  | 25 | 20 | 24 | 0.166 |
|  |  |  | 35 | 20 | 25 | 0.208 |
| 21 | B | — | 15 | 20 | — | — |

TABLE III-continued

Polymer Blend Ratios vs. Effect on Compaction and Supernatant Clarity

| Exp. No. | Flocculant | Ratio | g/l | No. of Tube Inversions | Centrifuge 5 Minutes % Volume Solids | Clarity of Supernatant 660 Microns |
|---|---|---|---|---|---|---|
|  |  |  | 25 | 20 | 18 | 1.680 |
|  |  |  | 35 | 20 | 18 | 0.253 |
| 22 | B/C | 3/1 | 15 | 20 | 20 | 0.017 |
|  |  |  | 25 | 20 | 19 | 0.672 |
|  |  |  | 35 | 20 | 19 | 0.152 |
| 23 | B/C | 1/1.5 | 15 | 20 | 18 | 1.530 |
|  |  |  | 25 | 20 | 20 | 0.198 |
|  |  |  | 35 | 20 | 20 | 0.114 |
| 24 | B/C | 1/3 | 15 | 20 | 20 | 0.314 |
|  |  |  | 25 | 20 | 20 | 0.260 |
|  |  |  | 35 | 20 | 20 | 0.069 |
| 25 | B/C | 1/7 | 15 | 20 | 20 | 0.306 |
|  |  |  | 25 | 20 | 20 | 0.103 |
|  |  |  | 35 | 20 | 23 | 0.172 |
| 26 | B/C | 1/30 | 15 | 20 | 24 | 0.299 |
|  |  |  | 25 | 20 | 24 | 0.125 |
|  |  |  | 35 | 20 | 25 | 0.298 |
| 27 | A/C | 3/1 | 10 | 20 | 20 | 0.479 |
|  |  |  | 15 | 20 | 22 | 0.098 |
|  |  |  | 20 | 20 | 19 | 0.119 |
|  |  |  | 25 | 20 | 20 | 0.069 |
| 28 | A/C | 1/3 | 10 | 20 | 23 | 0.176 |
|  |  |  | 12.5 | 20 | 21 | 0.058 |
|  |  |  | 15 | 20 | 20 | 0.070 |
|  |  |  | 17.5 | 20 | 20 | 0.034 |
|  |  |  | 20 | 20 | 20 | 0.053 |
| 29 | A/C | 1/30 | 15 | 20 | 25 | 0.046 |
|  |  |  | 20 | 20 | 23 | 0.031 |
|  |  |  | 25 | 20 | 23 | 0.039 |
| 30 | B/C | 3/1 | 10 | 20 | — | — |
|  |  |  | 12.5 | 20 | — | 0.484 |
|  |  |  | 15 | 20 | — | 0.194 |
|  |  |  | 17.5 | 20 | — | 0.135 |
|  |  |  | 20 | 20 | — | 0.095 |
| 31 | B/C | 1/3 | 10 | 20 | — | 0.253 |
|  |  |  | 12.5 | 20 | 20 | 0.124 |
|  |  |  | 15 | 20 | 19 | 0.106 |
|  |  |  | 17.5 | 20 | 19 | 0.063 |
|  |  |  | 20 | 20 | 20 | 0.066 |
| 32 | B/C | 1/30 | 10 | 20 | 24 | 0.138 |
|  |  |  | 12.5 | 20 | 23 | 0.073 |
|  |  |  | 15 | 20 | 22 | 0.056 |
|  |  |  | 17.5 | 20 | 23 | 0.043 |
|  |  |  | 20 | 20 | 23 | 0.031 |
| 33 | C | — | 10 | 20 | 34 | 0.563 |
|  |  |  | 15 | 20 | 31 | 0.340 |
|  |  |  | 17.5 | 20 | 31 | 0.319 |
|  |  |  | 20.0 | 20 | 30 | 0.290 |
|  |  |  | 22.5 | 20 | 30 | 0.095 |
|  |  |  | 25 | 20 | 30 | 0.103 |
| 34 | A | — | 15 | 20 | 20 | 0.253 |
|  |  |  | 17.5 | 20 | 20 | 0.225 |
|  |  |  | 20 | 20 | 19 | 0.154 |
| 35 | A/C | 3/1 | 10 | 20 | 23 | 0.932 |
|  |  |  | 12.5 | 20 | 21 | 0.244 |
|  |  |  | 15 | 20 | 21 | 0.202 |
|  |  |  | 17.5 | 20 | 21 | 0.096 |
|  |  |  | 20 | 20 | 22 | 0.146 |
| 36 | A/C | 1.3/1 | 10 | 20 | 21 | 0.367 |
|  |  |  | 12.5 | 20 | 22 | 0.237 |
|  |  |  | 15 | 20 | 20 | 0.150 |
|  |  |  | 17.5 | 20 | 22 | 0.089 |
|  |  |  | 20 | 20 | 21 | 0.118 |
| 37 | A/C | 1/1.5 | 10 | 20 | 23 | 0.329 |
|  |  |  | 12.5 | 20 | 22 | 0.207 |
|  |  |  | 15 | 20 | 20 | 0.166 |
|  |  |  | 17.5 | 20 | 21 | 0.102 |
|  |  |  | 20 | 20 | 21 | 0.109 |
| 38 | A/C | 1/3 | 15 | 20 | 22 | 0.145 |
|  |  |  | 17.5 | 20 | 22 | 0.177 |
|  |  |  | 20 | 20 | 21 | 0.072 |
| 39 | B | — | 15 | 20 | 21 | 0.796 |
|  |  |  | 17.5 | 20 | 22 | 0.298 |
|  |  |  | 20 | 20 | 20 | 0.184 |
| 40 | B/C | 3/1 | 10 | 20 | 23 | 0.932 |
|  |  |  | 12.5 | 20 | 21 | 0.244 |
|  |  |  | 15 | 20 | 21 | 0.202 |
|  |  |  | 17.5 | 20 | 21 | 0.096 |
|  |  |  | 20 | 20 | 22 | 0.146 |
| 41 | B/C | 1.3/1 | 10 | 20 | 21 | 0.367 |
|  |  |  | 12.5 | 20 | 22 | 0.237 |
|  |  |  | 15 | 20 | 20 |  |
|  |  |  | 17.5 | 20 | 19 | 0.129 |
| 42 | B/C | 1/1.5 | 10 | 20 | 20 | 0.742 |
|  |  |  | 12.5 | 20 | 20 | 0.232 |
|  |  |  | 15 | 20 | 19 | 0.176 |
|  |  |  | 17.5 | 20 | 19 | 0.125 |
|  |  |  | 20 | 20 | 20 | 0.120 |
| 43 | B/C | 1/3 | 15 | 20 | 20 | 0.184 |
|  |  |  | 17.5 | 20 | 20 | 0.106 |
|  |  |  | 20 | 20 | 20 | 0.095 |
| 44 | C | — | 10 | 20 | 30 | 0.462 |
|  |  |  | 12.5 | 20 | 30 | 0.388 |
|  |  |  | 15 | 20 | 29 | 0.369 |
|  |  |  | 17.5 | 20 | 30 | 0.365 |
|  |  |  | 20 | 20 | 32 | 0.348 |
|  |  |  | 22.5 | 20 | 32 | 0.345 |
| 45 | A/C | 3/1 | 12.5 | 20 | 18 | 0.859 |
|  |  |  | 15 | 20 | 19 | 0.565 |
|  |  |  | 17.5 | 20 | 19 | 0.403 |
|  |  |  | 20 | 20 | 18 | 0.306 |
|  |  |  | 22.5 | 20 | 20 | 0.263 |
|  |  |  | 25 | 20 | 21 | 0.233 |
| 46 | A/C | 1.3/1 | 12.5 | 20 | 20 | 0.481 |
|  |  |  | 15 | 20 | 20 | 0.390 |
|  |  |  | 17.5 | 20 | 20 | 0.276 |
|  |  |  | 20 | 20 | 20 | 0.259 |
|  |  |  | 22.5 | 20 | 22 | 0.219 |
|  |  |  | 25 | 20 | 22 | 0.188 |
| 47 | A/C | 1/1.5 | 12.5 | 20 | 21 | 0.498 |
|  |  |  | 15 | 20 | 21 | 0.388 |
|  |  |  | 17.5 | 20 | 21 | 0.318 |
|  |  |  | 20 | 20 | 22 | 0.288 |
|  |  |  | 22.5 | 20 | 22 | 0.231 |
|  |  |  | 25 | 20 | 23 | 0.251 |
| 48 | A/C | 1/3 | 12.5 | 20 | 20 | 0.331 |
|  |  |  | 15 | 20 | 21 | 0.282 |
|  |  |  | 17.5 | 20 | 22 | 0.253 |
|  |  |  | 20 | 20 | 23 | 0.140 |
|  |  |  | 22.5 | 20 | 24 | 0.201 |
|  |  |  | 25 | 20 | 25 | 0.224 |
| 49 | B/C | 3/1 | 12.5 | 20 | 20 | — |
|  |  |  | 15 | 20 | 18 | 0.656 |
|  |  |  | 17.5 | 20 | 18 | 0.148 |
|  |  |  | 20 | 20 | 19 | 0.381 |
|  |  |  | 22.5 | 20 | 18 | 0.197 |
|  |  |  | 25 | 20 | 19 | 0.327 |
| 50 | B/C | 1.3/1 | 12.5 | 20 | 17 | 1.01 |
|  |  |  | 15 | 20 | 18 | 0.505 |
|  |  |  | 17.5 | 20 | 18 | 0.321 |
|  |  |  | 20 | 20 | 18 | 0.272 |
|  |  |  | 22.5 | 20 | 19 | 0.208 |
|  |  |  | 25 | 20 | 20 | 0.205 |
| 51 | B/C | 1/1.5 | 12.5 | 20 | 18 | 0.522 |
|  |  |  | 15 | 20 | 19 | 0.331 |
|  |  |  | 17.5 | 20 | 20 | 0.243 |
|  |  |  | 20 | 20 | 19 | 0.173 |
|  |  |  | 22.5 | 20 | 20 | 0.145 |
|  |  |  | 25 | 20 | 19 | 0.130 |
| 52 | B/C | 1/3 | 12.5 | 20 | 20 | 0.299 |
|  |  |  | 15 | 20 | 20 | 0.240 |
|  |  |  | 17.5 | 20 | 20 | 0.166 |
|  |  |  | 20 | 20 | 20 | 0.155 |
|  |  |  | 22.5 | 20 | 21 | 0.152 |
|  |  |  | 25 | 20 | 22 | 0.160 |
| 53 | A/C | 3/1 | 16 | 20 | 21 | 0.266 |
|  |  |  | 18 | 20 | 22 | 0.303 |
|  |  |  | 20 | 20 | 20 | 0.195 |

TABLE III-continued

Polymer Blend Ratios vs. Effect on Compaction and Supernatant Clarity

| Exp. No. | Flocculant | Ratio | g/l | No. of Tube Inversions | Centrifuge 5 Minutes % Volume Solids | Clarity of Supernatant 660 Microns |
|---|---|---|---|---|---|---|
|  |  |  | 22 | 20 | 20 | 0.345 |
|  |  |  | 24 | 20 | 20.5 | 0.248 |
| 54 | A/C | 1/1.5 | 16 | 20 | 21.5 | 0.282 |
|  |  |  | 18 | 20 | 22 | 0.296 |
|  |  |  | 20 | 20 | 21 | 0.177 |
|  |  |  | 22 | 20 | 20 | 0.209 |
|  |  |  | 24 | 20 | 20.5 | 0.177 |
| 55 | A/C | 1/3 | 16 | 20 | 21 | 0.082 |
|  |  |  | 18 | 20 | 22.5 | 0.065 |
|  |  |  | 20 | 20 | 22 | 0.090 |
|  |  |  | 22 | 20 | 21 | 0.054 |
|  |  |  | 24 | 20 | 22 | 0.031 |
| 56 | A/C | 1/7 | 16 | 20 | 23 | 0.222 |
|  |  |  | 18 | 20 | 23 | 0.058 |
|  |  |  | 20 | 20 | 22.5 | 0.016 |
|  |  |  | 22 | 20 | 23 | 0.032 |
|  |  |  | 24 | 20 | 24 | 0.010 |
| 57 | A/C | 1/30 | 16 | 20 | 26 | 0.290 |
|  |  |  | 18 | 20 | 25 | 0.123 |
|  |  |  | 20 | 20 | 25 | 0.077 |
|  |  |  | 22 | 20 | 25 | 0.036 |
|  |  |  | 24 | 20 | 25 | 0.032 |
| 58 | B/C | 3/1 | 16 | 20 | 20 | 0.171 |
|  |  |  | 18 | 20 | 20 | 0.145 |
|  |  |  | 20 | 20 | 20 | 0.151 |
|  |  |  | 22 | 20 | 20 | 0.117 |
|  |  |  | 24 | 20 | 20 | 0.070 |
| 59 | B/C | 1/1.5 | 16 | 20 | 20 | 0.146 |
|  |  |  | 18 | 20 | 20 | 0.120 |
|  |  |  | 20 | 20 | 20 | 0.115 |
|  |  |  | 22 | 20 | 20 | 0.113 |
|  |  |  | 24 | 20 | 20 | 0.102 |
| 60 | B/C | 1/3 | 16 | 20 | 20 | 0.162 |
|  |  |  | 18 | 20 | 20 | 0.103 |
|  |  |  | 20 | 20 | 20 | 0.095 |
|  |  |  | 22 | 20 | 19.5 | 0.093 |
|  |  |  | 24 | 20 | 19.5 | 0.074 |
| 61 | B/C | 1/7 | 16 | 20 | 20.5 | — |
|  |  |  | 18 | 20 | 20.5 | 0.037 |
|  |  |  | 20 | 20 | 20 | 0.039 |
|  |  |  | 22 | 20 | 21.5 | 0.041 |
|  |  |  | 24 | 20 | 21.5 | 0.034 |
| 62 | B/C | 1/30 | 16 | 20 | 25 | 0.283 |
|  |  |  | 18 | 20 | 24 | 0.102 |
|  |  |  | 20 | 20 | 24 | 0.100 |
|  |  |  | 22 | 20 | 25 | 0.059 |
|  |  |  | 24 | 20 | 24 | 0.029 |

Table IV reflects the results of increasing the polymer blend dosage rate in Examples 63–72. As can be seen, upon treating an enzyme fermentation broth, increased blend dosages results in magnificent clarity values as low as 0.018 although compaction values are somewhat sacrificed.

In Examples 73–81, an enzyme broth is treated and at rather low dosage rates, the combined compaction/clarity values are considered acceptable.

TABLE IV

Polymer Blend Effect on Compaction and Supernatant Clarity on an Enzyme Broth

| Exp. No. | Flocculant | Ratio | g/l Flocculant | No. of Tube Inversions | Centrifuge 5 Minutes % Volume Solids | Clarity of Supernatant 660 Microns |
|---|---|---|---|---|---|---|
| 63 | A/C | 3/1 | — | — | — | — |
|  |  |  | 40 | 20 | 32 | — |
|  |  |  | 50 | 20 | 30 | 0.506 |
| 64 | A/C | 1/1.5 | 30 | 20 | 30 | 1.300 |
|  |  |  | 40 | 20 | 30 | 0.088 |
|  |  |  | 50 | 20 | — | — |
| 65 | A/C | 1/3 | 30 | 20 | — | — |
|  |  |  | 40 | 20 | 30 | 0.140 |
|  |  |  | 50 | 20 | 31 | 0.096 |
| 66 | A/C | 1/7 | — | — | — | — |
|  |  |  | 40 | 20 | 30 | 0.074 |
|  |  |  | 50 | 20 | 30 | 0.040 |
| 67 | A/C | 1/3 | — | — | — | — |
|  |  |  | 40 | 20 | 30 | 0.056 |
|  |  |  | 50 | 20 | 28 | 0.018 |
| 68 | B/C | 3/1 | 40 | 20 | 28 | — |
|  |  |  | 50 | 20 | 30 | 0.291 |
| 69 | B/C | 1/1.5 | 40 | 20 | 31 | 1.580 |
|  |  |  | 50 | 20 | 29 | 0.172 |
| 70 | B/C | 1/3 | 40 | 20 | 30 | 0.280 |
|  |  |  | 50 | 20 | 30 | 0.052 |
| 71 | B/C | 1/7 | 40 | 20 | 30 | 0.142 |
|  |  |  | 50 | 20 | 30 | 0.044 |
| 72 | B/C | 1/30 | 30 | 20 | 30 | 0.063 |
|  |  |  | 40 | 20 | 30 | 0.027 |
|  |  |  | 50 | 20 | — | — |
| 73 | C | — | 10 | 20 | 54 | — |
|  |  |  | 12.5 | 20 | 48 | — |
|  |  |  | 15 | 20 | 45 | — |
|  |  |  | 17.5 | 20 | 45 | 1.00 |
|  |  |  | 20 | 20 | 37 | 0.042 |
|  |  |  | 22.5 | 20 | 35 | 0.032 |
| 74 | A/C | 1/3 | 22.5 | 20 | 32 | — |
|  |  |  | 25 | 20 | 30 | 0.258 |
|  |  |  | 27.5 | 20 | 30 | 0.178 |

TABLE IV-continued

Polymer Blend Effect on Compaction and Supernatant Clarity on an Enzyme Broth

| Exp. No. | Flocculant | Ratio | g/l Flocculant | No. of Tube Inversions | Centrifuge 5 Minutes % Volume Solids | Clarity of Supernatant '660 Microns |
|---|---|---|---|---|---|---|
| 75 | A/C | 1/7 | 15 | 20 | 33 | 0.375 |
| | | | 20 | 20 | 29 | 0.156 |
| | | | 22.5 | 20 | 28 | 0.178 |
| | | | 25 | 20 | 28 | 0.089 |
| | | | 27.5 | 20 | 26 | 0.105 |
| 76 | A/C | 1/11.5 | 15 | 20 | 30 | 0.154 |
| | | | 20 | 20 | 28 | 0.169 |
| | | | 22.5 | 20 | 27 | 0.199 |
| | | | 25 | 20 | 27 | 0.091 |
| | | | 27.5 | 20 | 27 | 0.126 |
| 77 | A/C | 1/30 | 15 | 20 | 30 | 0.124 |
| | | | 20 | 20 | 28 | 0.189 |
| | | | 22.5 | 20 | 27 | 0.265 |
| | | | 25 | 20 | 27 | 0.127 |
| | | | 27.5 | 20 | 27 | 0.141 |
| 78 | B/C | 1/3 | 22.5 | 20 | 29 | — |
| | | | 25 | 20 | 30 | — |
| | | | 27.5 | 20 | 30 | — |
| 79 | B/C | 1/7 | 15 | 20 | 31 | — |
| | | | 20 | 20 | 31 | — |
| | | | 22.5 | 20 | 31 | 0.493 |
| | | | 25 | 20 | 28 | 0.227 |
| | | | 27.5 | 20 | 28 | 0.168 |
| 80 | B/C | 1/11.5 | 15 | 20 | 30 | — |
| | | | 20 | 20 | 31 | 0.235 |
| | | | 22.5 | 20 | 30 | 0.152 |
| | | | 25 | 20 | 26 | 0.113 |
| | | | 27.5 | 20 | 28 | 0.116 |
| 81 | B/C | 1/30 | 15 | 20 | 30 | 0.161 |
| | | | 20 | 20 | 28 | 0.147 |
| | | | 22.5 | 20 | 26 | 0.187 |
| | | | 25 | 20 | 25 | 0.085 |
| | | | 27.5 | 20 | 26 | 0.136 |

The effects of mixing are shown in Table V. An enzyme broth is treated with the blends, the clinical test tube being inverted from 10 to 100 times in Examples 82 and 83. As can be seen, undue agitation appears to deleteriously affect mechanical break-up of flocculated particles, leading to the creation of many fines. The same trend can be seen in Examples 84-89, in Examples 90-95 and in Examples 96-107.

TABLE V

Mixing Factor vs. Compaction and Supernatant Clarity

| Exp. No. | Flocculant | Ratio | g/l Flocculant | No. of Tube Inversions | Centrifuge 5 Minutes % Volume Solids | Clarity of Supernatant 660 Microns |
|---|---|---|---|---|---|---|
| 82 | A/C | 1.3/1 | 20 | 10 | 21 | 0.162 |
| | | | 20 | 20 | 20 | 0.195 |
| | | | 20 | 30 | 20 | 0.201 |
| | | | 20 | 50 | 20 | 0.284 |
| | | | 20 | 75 | 20 | 0.363 |
| | | | 20 | 100 | 20 | 0.397 |
| 83 | B/C | 1.3/1 | 20 | 10 | 23 | 0.143 |
| | | | 20 | 20 | 21 | 0.225 |
| | | | 20 | 30 | 20 | 0.179 |
| | | | 20 | 50 | 18 | 0.222 |
| | | | 20 | 75 | 20 | 0.347 |
| | | | 20 | 100 | 20 | 0.534 |
| 84 | A/C | 1/1.5 | 16 | 20 | 21 | 0.198 |
| | | | 18 | 20 | 21.5 | 0.085 |
| | | | 20 | 20 | 21 | 0.079 |
| | | | 22 | 20 | 20 | 0.058 |
| | | | 24 | 20 | 20.5 | 0.047 |
| 85 | A/C | 1/1.5 | 16 | 40 | 22 | 0.374 |
| | | | 18 | 40 | 20.5 | 0.229 |
| | | | 20 | 40 | 21 | 0.078 |
| | | | 22 | 40 | 21 | 0.102 |
| | | | 24 | 40 | 20 | 0.074 |
| 86 | A/C | 1/1.5 | 16 | 75 | 22 | 0.358 |
| | | | 18 | 75 | 24 | 0.441 |
| | | | 20 | 75 | 22 | 0.655 |
| | | | 22 | 75 | 22 | 0.400 |
| | | | 24 | 75 | 22 | 0.293 |
| 87 | B/C | 1/1.5 | 16 | 20 | 21 | 0.529 |

TABLE V-continued

Mixing Factor vs. Compaction and Supernatant Clarity

| Exp. No. | Flocculant | Ratio | g/l Flocculant | No. of Tube Inversions | Centrifuge 5 Minutes % Volume Solids | Clarity of Supernatant 660 Microns |
|---|---|---|---|---|---|---|
|  |  |  | 18 | 20 | 20.5 | 0.360 |
|  |  |  | 20 | 20 | 20 | 0.464 |
|  |  |  | 22 | 20 | 20.5 | 0.365 |
|  |  |  | 24 | 20 | 20 | 0.435 |
| 88 | B/C | 1/1.5 | 16 | 40 | 20 | 0.233 |
|  |  |  | 18 | 40 | 20 | 0.095 |
|  |  |  | 20 | 40 | 19.5 | 0.078 |
|  |  |  | 22 | 40 | 20 | 0.102 |
|  |  |  | 24 | 40 | 19.5 | 0.107 |
| 89 | B/C | 1/1.5 | 16 | 75 | 20.5 | 0.404 |
|  |  |  | 18 | 75 | 19.5 | 0.338 |
|  |  |  | 20 | 75 | 21 | 0.147 |
|  |  |  | 22 | 75 | 20.5 | 0.351 |
|  |  |  | 24 | 75 | 20 | 0.101 |
| 90 | A/C | 1/1.5 | 16 | 20 | 22.5 | 0.301 |
|  |  |  | 18 | 20 | 23 | 0.164 |
|  |  |  | 20 | 20 | 23.5 | 0.125 |
|  |  |  | 22 | 20 | 24 | 0.114 |
|  |  |  | 24 | 20 | 24 | 0.094 |
| 91 | A/C | 1/1.5 | 16 | 40 | 24 | 0.335 |
|  |  |  | 18 | 40 | 23 | 0.318 |
|  |  |  | 20 | 40 | 22.5 | 0.220 |
|  |  |  | 22 | 40 | 22.5 | 0.112 |
|  |  |  | 24 | 40 | 22.5 | 0.059 |
| 92 | A/C | 1/1.5 | 16 | 75 | 22.5 | 1.503 |
|  |  |  | 18 | 75 | 22.5 | 1.426 |
|  |  |  | 20 | 75 | 23 | 0.834 |
|  |  |  | 22 | 75 | 22.5 | 0.280 |
|  |  |  | 24 | 75 | 22.5 | 0.338 |
| 93 | B/C | 1/1.5 | 16 | 20 | 22 | 0.795 |
|  |  |  | 18 | 20 | 22.5 | 0.219 |
|  |  |  | 20 | 20 | 23 | 0.184 |
|  |  |  | 22 | 20 | 24 | 0.153 |
|  |  |  | 24 | 20 | 23 | 0.145 |
| 94 | B/C | 1/1.5 | 16 | 40 | 21.5 | 0.696 |
|  |  |  | 18 | 40 | 22 | 0.377 |
|  |  |  | 20 | 40 | 22 | 0.248 |
|  |  |  | 22 | 40 | 22.5 | 0.208 |
|  |  |  | 24 | 40 | 22 | 0.147 |
| 95 | B/C | 1/1.5 | 16 | 75 | 20 | — |
|  |  |  | 18 | 75 | 20.5 | 1.927 |
|  |  |  | 20 | 75 | 22.5 | 1.504 |
|  |  |  | 22 | 75 | 20.5 | 1.303 |
|  |  |  | 24 | 75 | 22 | 0.808 |
| 96 | A/C | 3/1 | 16 | 40 | 22.5 | 0.663 |
|  |  |  | 18 | 40 | 22.5 | 0.661 |
|  |  |  | 20 | 40 | 22 | 0.314 |
|  |  |  | 22 | 40 | 22 | 0.064 |
|  |  |  | 24 | 40 | 22.5 | 0.216 |
| 97 | A/C | 3/1 | 16 | 75 | 22.5 | 1.18 |
|  |  |  | 18 | 75 | 21.5 | 0.823 |
|  |  |  | 20 | 75 | 23 | 0.598 |
|  |  |  | 22 | 75 | 21 | 0.570 |
|  |  |  | 24 | 75 | 22.5 | 0.107 |
| 98 | A/C | 1/1.5 | 16 | 40 | 23 | 0.515 |
|  |  |  | 18 | 40 | 22 | 0.420 |
|  |  |  | 20 | 40 | 23.5 | 0.210 |
|  |  |  | 22 | 40 | 21 | 0.077 |
|  |  |  | 24 |  | 22 | 0.159 |
| 99 | A/C | 1/1.5 | 16 | 75 | 23.5 | 0.688 |
|  |  |  | 18 | 75 | 22.5 | 0.586 |
|  |  |  | 20 | 75 | 22 | 0.366 |
|  |  |  | 22 | 75 | 22 | 0.295 |
|  |  |  | 24 | 75 | 22.0 | 0.084 |
| 100 | A/C | 1/3 | 16 | 40 | 23 | 0.293 |
|  |  |  | 18 | 40 | 22.5 | 0.183 |
|  |  |  | 20 | 40 | 25 | 0.087 |
|  |  |  | 22 | 40 | 25 | 0.071 |
|  |  |  | 24 | 40 | 25 | 0.042 |
| 101 | A/C | 1/3 | 16 | 75 | 23 | 0.285 |
|  |  |  | 18 | 75 | 25 | 0.252 |
|  |  |  | 20 | 75 | 24 | 0.117 |
|  |  |  | 22 | 75 | 25 | 0.179 |
|  |  |  | 24 | 75 | 25 | 0.063 |
| 102 | B/C | 3/1 | 16 | 40 | 22 | 0.551 |
|  |  |  | 18 | 40 | 20 | 0.310 |
|  |  |  | 20 | 40 | 21 | 0.152 |

TABLE V-continued

Mixing Factor vs. Compaction and Supernatant Clarity

| Exp. No. | Flocculant | Ratio | g/l Flocculant | No. of Tube Inversions | Centrifuge 5 Minutes % Volume Solids | Clarity of Supernatant 660 Microns |
|---|---|---|---|---|---|---|
| | | | 22 | 40 | 20 | 0.088 |
| | | | 24 | 40 | 22 | 0.093 |
| 103 | B/C | 3/1 | 16 | 75 | 20 | 0.538 |
| | | | 18 | 75 | 21 | 0.295 |
| | | | 20 | 75 | 21 | 0.223 |
| | | | 22 | 75 | 19.5 | 0.120 |
| | | | 24 | 75 | | |
| 104 | B/C | 1/1.5 | 16 | 40 | 22 | 0.275 |
| | | | 18 | 40 | 20.5 | 0.088 |
| | | | 20 | 40 | 20 | 0.065 |
| | | | 22 | 40 | 20 | 0.038 |
| | | | 24 | 40 | 21.5 | 0.052 |
| 105 | B/C | 1/1.5 | 16 | 75 | 21.5 | 0.058 |
| | | | 18 | 75 | 21.5 | 0.064 |
| | | | 20 | 75 | 21 | 0.143 |
| | | | 22 | 75 | 20 | 0.098 |
| | | | 24 | 75 | 22 | 0.095 |
| 106 | B/C | 1/3 | 16 | 40 | 21.5 | 0.069 |
| | | | 18 | 40 | 20.5 | 0.051 |
| | | | 20 | 40 | 22 | 0.042 |
| | | | 22 | 40 | 22 | 0.046 |
| | | | 24 | | 22.5 | 0.059 |
| 107 | B/C | 1/3 | 16 | 75 | 22 | 0.338 |
| | | | 18 | 75 | 22 | 0.256 |
| | | | 20 | 75 | 23 | 0.055 |
| | | | 22 | 75 | 22.5 | 0.079 |
| | | | 24 | 75 | 22.5 | 0.052 |

The broad effect of the blends of polymers of the present invention on an enzyme broth is shown in Table VI. The overall tread again supports the unique results achieved by said blends.

TABLE VI

Polymer Blend Ratios vs. Affect on Compaction and Clarity of Supernatant at 40 Inversions

| Exp. No. | Flocculant | Ratio | g/l Flocculant | No. of Tube Inversions | Centrifuge 5 Minutes % Volume Solids | Clarity of Supernatant 660 Microns |
|---|---|---|---|---|---|---|
| 108 | A/C | 3/1 | 16 | 40 | 22 | 0.406 |
| | | | 18 | 40 | 23 | 0.290 |
| | | | 20 | 40 | 22.5 | 0.189 |
| | | | 22 | 40 | 22 | 0.141 |
| | | | 24 | 40 | 22 | 0.182 |
| 109 | A/C | 1/1.5 | 16 | 40 | 24 | 0.335 |
| | | | 18 | 40 | 23 | 0.318 |
| | | | 20 | 40 | 22.5 | 0.220 |
| | | | 22 | 40 | 22.5 | 0.112 |
| | | | 24 | 40 | 22.5 | 0.059 |
| 110 | A/C | 1/3 | 16 | 40 | 24.5 | 0.119 |
| | | | 18 | 40 | 24 | 0.115 |
| | | | 20 | 40 | 24.5 | 0.082 |
| | | | 22 | 40 | 25 | 0.162 |
| | | | 24 | 40 | 25.5 | 0.207 |
| 111 | A/C | 1/7 | 16 | 40 | 25 | 0.259 |
| | | | 18 | 40 | 25.5 | 0.064 |
| | | | 20 | 40 | 26 | 0.118 |
| | | | 22 | 40 | 27 | 0.106 |
| | | | 24 | 40 | 28.5 | 0.215 |
| 112 | A/C | 1/30 | 16 | 40 | 29 | 0.123 |
| | | | 18 | 40 | 29 | 0.101 |
| | | | 20 | 40 | 29 | 0.106 |
| | | | 22 | 40 | 30 | 0.104 |
| | | | 24 | 40 | 30 | 0.066 |
| 113 | B/C | 3/1 | 16 | 40 | 20 | 0.860 |
| | | | 18 | 40 | 20.5 | 0.482 |
| | | | 20 | 40 | 20 | 0.356 |
| | | | 22 | 40 | 20 | 0.301 |
| | | | 24 | 40 | 20 | 0.235 |
| 114 | B/C | 1/1.5 | 16 | 40 | 21.5 | 0.696 |
| | | | 18 | 40 | 22 | 0.377 |
| | | | 20 | 40 | 22 | 0.248 |
| | | | 22 | 40 | 22.5 | 0.208 |

TABLE VI-continued

Polymer Blend Ratios vs. Affect on Compaction and Clarity of Supernatant at 40 Inversions

| Exp. No. | Flocculant | Ratio | g/l Flocculant | No. of Tube Inversions | Centrifuge 5 Minutes % Volume Solids | Clarity of Supernatant 660 Microns |
| --- | --- | --- | --- | --- | --- | --- |
|  |  |  | 24 | 40 | 22 | 0.147 |
| 115 | B/C | 1/3 | 16 | 40 | 22 | 0.057 |
|  |  |  | 18 | 40 | 21 | 0.096 |
|  |  |  | 20 | 40 | 22.5 | 0.062 |
|  |  |  | 22 | 40 | 22 | 0.066 |
|  |  |  | 24 | 40 | 22 | 0.110 |
| 116 | B/C | 1/7 | 16 | 40 | 23.5 | 0.078 |
|  |  |  | 18 | 40 | 23.5 | 0.071 |
|  |  |  | 20 | 40 | 24.5 | 0.068 |
|  |  |  | 22 | 40 | 25 | 0.062 |
|  |  |  | 24 | 40 | 25 | 0.019 |
| 117 | B/C | 1/30 | 16 | 40 | 28.5 | 0.172 |
|  |  |  | 18 | 40 | 29 | 0.185 |
|  |  |  | 20 | 40 | 29.5 | 0.169 |
|  |  |  | 22 | 40 | 29.5 | 0.157 |
|  |  |  | 24 | 40 | 30.5 | 0.145 |

We claim:

1. A process for the flocculation of an aqueous enzyme broth which comprises adding to said broth a flocculant comprising a mixture of (1) a Mannich acrylamide polymer and (2) a dimethyldiallylammonium halide polymer.

2. A process according to claim 1 wherein the ratio of (1) to (2) ranges from about 3:1 to about 1:30, by weight, respectively.

3. A process according to claim 1 wherein the ratio of (1) to (2) ranges from about 1:1.5 to about 1:7, by weight, respectively.

4. A process according to claim 1 wherein (1) is a Mannich homopolymer of acrylamide.

5. A process according to claim 1 wherein (1) is a Mannich copolymer of acrylamide containing 5-50% of a comonomer.

6. A process according to claim 1 wherein (1) contains 25-100 mol percent of dimethylaminomethyl groups.

7. A process according to claim 1 wherein (2) is a chloride.

8. A process according to claim 1 wherein (2) is polydimethyldiallylammonium chloride.

9. A process according to claim 1 wherein the enzyme is a protease.

10. A process according to claim 1 wherein from about 10 to 100 grams per liter of broth of polymer blend is added.

* * * * *